US009870721B2

(12) United States Patent
Savitsky et al.

(10) Patent No.: US 9,870,721 B2
(45) Date of Patent: Jan. 16, 2018

(54) SYSTEM AND METHOD FOR TEACHING BASIC ULTRASOUND SKILLS

(71) Applicants: Eric Savitsky, Malibu, CA (US); Gabriele Nataneli, Beverly Hills, CA (US); Dan Katz, Encino, CA (US); Kresimir Petrinec, Los Angeles, CA (US)

(72) Inventors: Eric Savitsky, Malibu, CA (US); Gabriele Nataneli, Beverly Hills, CA (US); Dan Katz, Encino, CA (US); Kresimir Petrinec, Los Angeles, CA (US)

( * ) Notice: Subject to any disclaimer, the term of this patent is extended or adjusted under 35 U.S.C. 154(b) by 135 days.

(21) Appl. No.: 14/109,706

(22) Filed: Dec. 17, 2013

(65) Prior Publication Data

US 2014/0170620 A1 Jun. 19, 2014

Related U.S. Application Data

(60) Provisional application No. 61/738,564, filed on Dec. 18, 2012.

(51) Int. Cl.
*G09B 23/28* (2006.01)
*A61B 8/00* (2006.01)

(52) U.S. Cl.
CPC ............ *G09B 23/286* (2013.01); *A61B 8/466* (2013.01)

(58) Field of Classification Search
CPC ....................................................... G09B 23/28
USPC ......................................................... 434/262
See application file for complete search history.

(56) References Cited

U.S. PATENT DOCUMENTS

| 5,609,485 | A | * | 3/1997 | Bergman | G01S 7/52055 |
| | | | | | 128/916 |
| 5,689,443 | A | * | 11/1997 | Ramanathan | A61B 8/00 |
| | | | | | 600/437 |
| 5,827,942 | A | * | 10/1998 | Madsen | G01S 7/5205 |
| | | | | | 73/1.82 |
| 6,063,030 | A | * | 5/2000 | Vara | A61B 8/468 |
| | | | | | 600/437 |
| 6,117,078 | A | * | 9/2000 | Lysyansky | G01S 7/52036 |
| | | | | | 434/262 |
| 6,193,657 | B1 | * | 2/2001 | Drapkin | A61B 8/0833 |
| | | | | | 434/262 |
| 6,468,212 | B1 | * | 10/2002 | Scott | A61B 8/00 |
| | | | | | 600/437 |
| 2002/0173721 | A1 | * | 11/2002 | Grunwald | A61B 8/00 |
| | | | | | 600/437 |
| 2005/0181342 | A1 | * | 8/2005 | Toly | G09B 23/30 |
| | | | | | 434/262 |
| 2006/0020204 | A1 | * | 1/2006 | Serra | A61B 8/0833 |
| | | | | | 600/437 |

(Continued)

*Primary Examiner* — Sam Yao
*Assistant Examiner* — Alvin Carlos
(74) *Attorney, Agent, or Firm* — Cislo & Thomas, LLP (57) ABSTRACT

A system and method that improves the speed and efficiency through which ultrasound practitioners acquire and develop essential basic ultrasound skills in a simulated environment without the need of actual patients or subjects. The system utilizes a simulator with an input device that manipulate a virtual transducer probe in a simulated 3D space to cut a slice through a basic shape. A 2D section of the cut plane is also displayed so that the practitioner can learn to relate 2D section with their 3D objects cut in cross-section.

17 Claims, 4 Drawing Sheets

(56) References Cited

U.S. PATENT DOCUMENTS

| | | | |
|---|---|---|---|
| 2007/0088213 A1* | 4/2007 | Poland | G01S 7/52084 600/437 |
| 2008/0187896 A1* | 8/2008 | Savitsky | G09B 23/28 434/272 |
| 2009/0043195 A1* | 2/2009 | Poland | A61B 8/00 600/437 |
| 2010/0055657 A1* | 3/2010 | Goble | G09B 23/286 434/262 |
| 2012/0179039 A1* | 7/2012 | Pelissier | A61B 8/4263 600/443 |

* cited by examiner

SYSTEM AND METHOD FOR TEACHING BASIC ULTRASOUND SKILLS

CROSS-REFERENCE TO RELATED APPLICATION

This patent application claims the benefit of U.S. Provisional Patent Application Ser. No. 61/738,564, entitled "System and Method for Teaching Basic Ultrasound Skills," filed Dec. 18, 2012, which application is incorporated in its entirety here by this reference.

TECHNICAL FIELD

This invention relates to a method and system for teaching practitioners how to effectively and efficiently use an ultrasound machine.

BACKGROUND

While a good understanding of ultrasonography requires thorough knowledge of anatomy and other related medical topics, basic proficiency with ultrasound scanning also requires mastery of several skills that transcend general medical knowledge. By way of example only, ultrasound practitioners should develop: a good understanding of how to relate the shape of three-dimensional (3D) objects to their respective two-dimensional (2D) sections (also known as slices or cuts); precise hand-eye coordination to understand how to move the ultrasound probe in physical space to explore a given 3D shape, while looking at the corresponding visual image on an ultrasound machine; an accurate understanding of scale, useful to relate ultrasound findings to the physical size of the objects undergoing ultrasound imaging; the ability to choose the correct image windows (locations) for placing the ultrasound probe in order to quickly decipher the 3D shape of the item being inspected; and the ability to rapidly and accurately acquire an optimal view (image) of an object or area of interest once an ideal image window (probe location) is attained, which requires highly refined and subtle probe manipulation skills.

These, and other related skills, will be referred to as basic ultrasound skills, in the current state of training, novices are presented directly with the complexity of real ultrasound images of human subjects and expected to acquire the above skills while also learning many other aspects of ultrasonography and clinical medicine at the same time. The problem is that ultrasound images of human subjects provide poor abstractions for basic ultrasound skills. An unsatisfactory understanding of these basic non-medical concepts will impede novices from mastering more advanced material.

Real ultrasound images of human subjects present at least the following challenges: the shape of anatomical structures is often complex and hard to conceptualize; the exact visible boundaries of anatomical regions are blurred and hard to identify; the images are compounded with noise and other artifacts specific to ultrasound imaging, such as shadows and reflections; images of human subjects often are dynamic (e.g., beating heart) or deform during a scan in response to physical compression of the body; the complexity of image window acquisition and subsequent image view optimization can overwhelm new learners.

Therefore, there is a need for a training system and method to efficiently and effectively improve the skill of the ultrasound practitioner without the need of actual patients or subjects.

SUMMARY

The invention of the present application is a system and method that improves the speed and efficiency through which new ultrasound practitioners acquire essential basic ultrasound skills in a simulated environment without the need of actual patients or subjects. One aspect of the present invention is to present new ultrasound practitioners with a collection of basic shapes that provide highly relevant abstractions of anatomic shapes and structures that they will encounter when studying real human anatomy with an ultrasound machine. Additionally, a simulated environment is designed in such a way that interactions with the system are an accurate representation of how a real ultrasound device operates. For example, new ultrasound practitioners will learn the image transducer array shape and depth based on transducer type selection. The simulated environment henceforth may be referred to as the simulator.

DETAILED DESCRIPTION OF THE INVENTION

The detailed description set forth below is connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
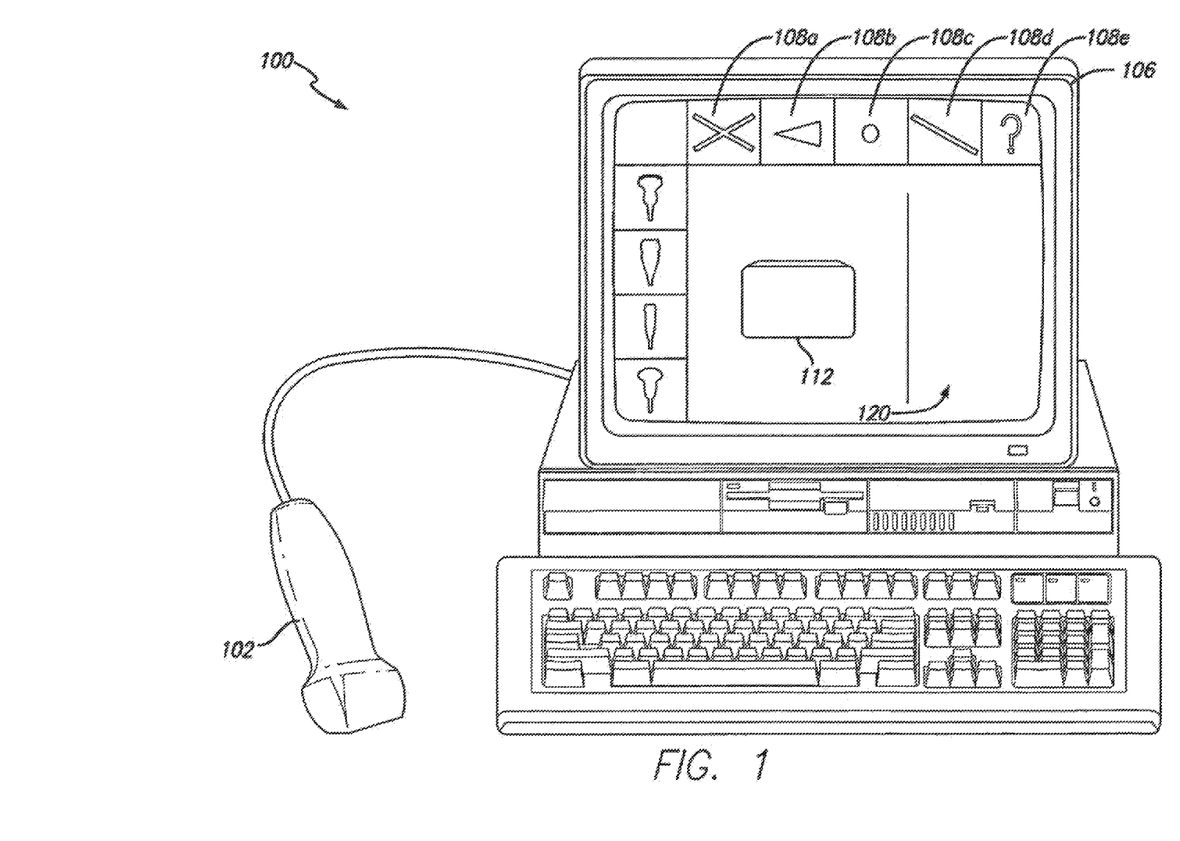
FIG. 1 shows an embodiment of a system of the present invention.

The invention of the present application relates to a training simulator system 100 (or simulator) and method for helping a practitioner achieve proficiency, and ultimately, mastery of basic skills is ultrasonography. A practitioner can be any person that uses an ultrasound machine, including, but not limited to, a physician, a physician's assistant, a nurse, a technician, a student, and the like. The simulator 100 comprises an input device 102 to control a virtual ultrasound probe 104 that lets the user define the position and/or orientation of the virtual ultrasound probe 104 in a virtual 3D space, a display device 106 that can present a perspective or orthographic representation of 3D geometry to the practitioner, a graphics engine capable of creating a 2D-image of a section of a given 3D shape to display on the display device, and a processor or other computational engine for calculating the section of a 3D shape in real time.

In use, the practitioner is situated in front of the display device 106 with control over the input device 102. The display device 106 may present the practitioner with a plurality of virtual basic shapes 108a-d having certain characteristics, such as its appearance, size, dimensions, whether the shape is dynamic (with moving features) or static, and the like.

Figure 2:
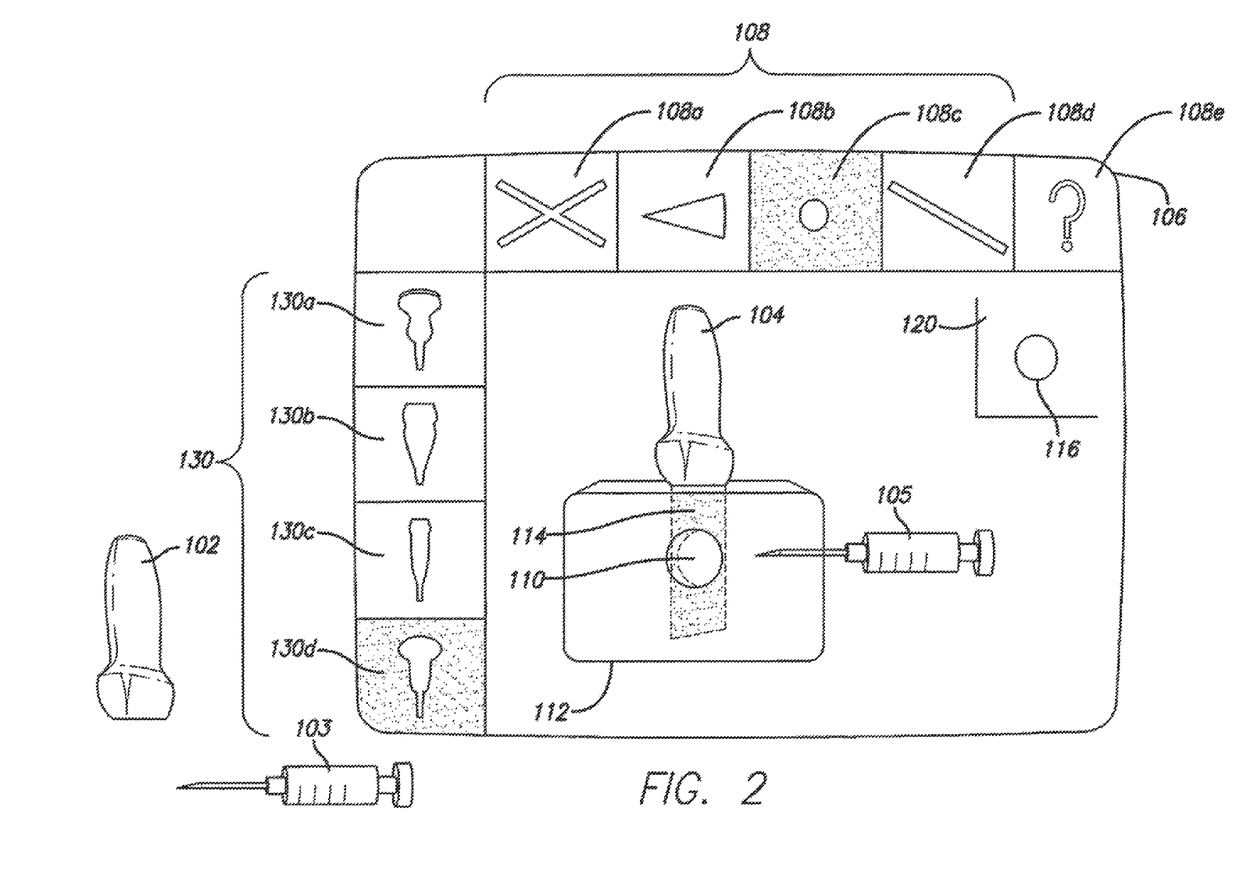
FIG. 2 shows as embodiment of the present invention with the virtual transducer probe cutting through a spherical basic shape, and a virtual needle.

The practitioner selects a virtual basic shape 108a-d from a list shown on the display device 106, for example, by using the input device 102. The virtual basic shape selected may depend on the anatomical structure the practitioner intends on examining. The shape should have an appearance that generally represents the anatomical structure being examined. Once the basic shape is selected, a 3D representation 110 of a virtual basic shape may be displayed on the display device 106 as shown in FIG. 2. In some embodiments, the basic shape may be displayed within an environment 112.

Once the basic shape or the anatomical structure has been selected, the practitioner then uses the input device 102, which represents a virtual ultrasound probe 104, to manipulate the position and/or orientation of the virtual ultrasound probe 104 in real-time relative to the selected basic shape 110 to simulate the movement of a real ultrasound probe and define an ultrasound slice through the selected basic shape 110 in 3D space. The virtual ultrasound probe 104 may be displayed as a transducer probe with virtual sound waves being emitted from, the transducer probe to define a scanning plane 114. By way of example only, the scanning plane 114 for a linear transducer probe may be depicted as a rectangular plane projecting away from the virtual transducer probe 104 and a scanning plane 114 for a curvilinear transducer probe may be depicted as a sector projecting away from the virtual transducer probe 104.

The input device 102 behaves in a manner that mimics closely to the manipulation of a real ultrasound probe and the displayed output provides a good understanding of how the scanning plane 114 of the ultrasound probe is oriented in 3D space. Being able to visualize the location, direction, and orientation of the sound waves (i.e. the scanning plane), the practitioner can now direct the sound waves into the selected basic shape 110 in the desired orientation and location to obtain an ultrasound slice 116 by moving the input device 102 accordingly.

As the practitioner alters the position and orientation of the scanning plane 114 in 3D space with the input device 102, the processor computes the section obtained by cutting the selected basic shape 110 with the scanning plane 114. The resulting section 116 is displayed on the display device 106 as a 2D image representing the section cut through by the scantling plane 114. The resulting section 116 may be displayed adjacent to the selected basic shape 110, for example, in a new window 120, as a split-screen, as a picture-in-picture, and the like. This trains the practitioner to be able to correlate 3D objects cut into sections with their corresponding 2D cross sections.

Input Device

The input device 102 can be embodied by any traditional means of interaction with a computer such as a mouse and keyboard, a trackball, a touch sensitive surface, gamepad, joystick, wireless controller and the like. In the preferred embodiment, the input device 102 is a motion-sensing device, such as a transducer frame with an accelerometer and input/output means. This causes the movement of the input device 102 to correlate directly with the movement and orientation of the virtual transducer probe 102 in real-time; thereby giving the practitioner the actual feel of using a real transducer probe.

Computational Engine

Computational engines, or processors, are used to execute software instructions. These are coupled directly or indirectly to memory elements. The memory elements can include local memory employed during actual execution of the program code, balk storage, and cache memories that provide temporary storage of at least some program code in order to reduce the number of times code is retrieved front bulk storage during execution. Advanced computational engines are available to practitioners at low cost and can be integrated in a variety of devices ranging from mobile phones to workstations connected to large screens.

Graphics Engine

The software uses a graphics engine with basic capabilities for displaying 3D and 2D objects on screen. The graphics engine should be able to render and display the virtual tools, shapes, and any effects respired by the software. Such tools are widely available as reusable software components to developers and can be integrated into a new application inexpensively.

Software

The software is a computer program product accessible from a computer-usable or computer-readable medium providing program code for use by or in connection with a computer or any instruction execution system, such as the computational engine or processor. For the purposes of this description, a computer-usable or computer-readable medium can be any apparatus that can contain, store, communicate, propagate, or transport the program for use by or in connection with the instruction execution system, apparatus, or device.

The computer-readable medium can be an electronic, magnetic, optical, electromagnetic, infrared, or semiconductor system (or apparatus or device) or a propagation medium. Examples of a computer-readable medium comprise a semiconductor or solid-state memory, magnetic tape, a removable computer diskette, a random access memory (RAM), a read-only memory (ROM), a rigid magnetic disk and an optical disk. Current examples of optical disks comprise compact disk-read only memory (CD-ROM), compact disk-read/write (CD-R/W) and DVD.

The processor should perform at least the following basic operations: display an interactive graphical user interface; acquire input from the input device 102; display the orientation of the scanning plane 114 in relation to the basic shape 110 in 3D space using a perspective or orthographic projection of the 3D scene on a display device 106 (including stereoscopic 3D displays or virtual reality systems); change the orientation of the scanning plane 114 based on the input from the input device; compute the section 116 of the basic shapes 110 when the scanning plane 114 cuts it; and display a visual representation of the section 116 on the display device 106.

Figure 4:
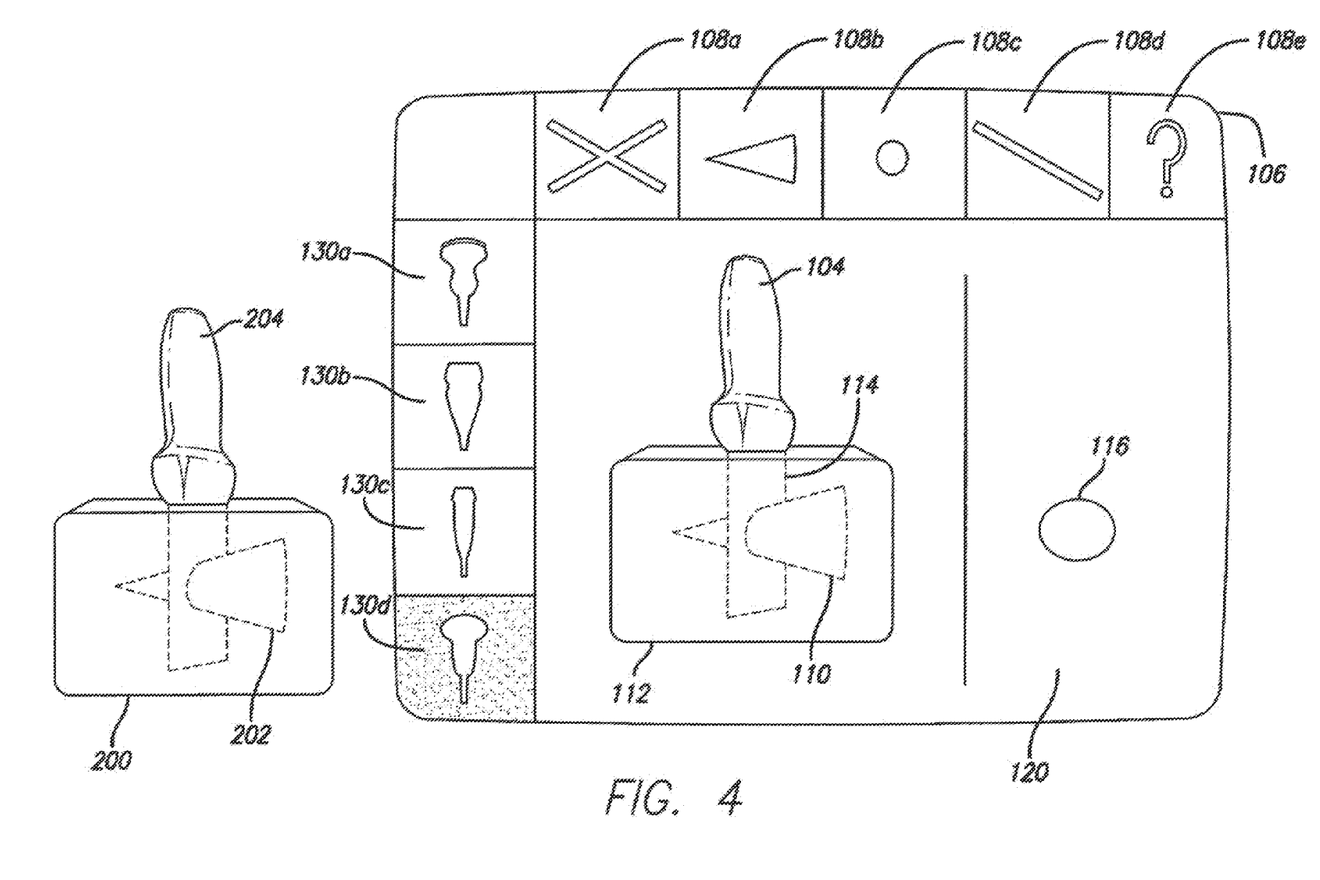
FIG. 4 shows at embodiment of the present invention with the virtual transducer probe mimicking the input device scanning a physical box imitating a structure being scanned by an ultrasound machine.

The section 116 defined by cutting through the basic shape 110 with the scanning plane 114 can the defined in several ways. For example, the geometry of the basic shape 110 may be defined using any known 3D modeling representation (e.g., 3D mesh, constructive solid geometry, non-uniform rational B-spline, etc.) and the section 116 computed by using known algorithms of computational geometry or by simulating the physics of ultrasound directly. In some embodiments, the geometry of the basic shape 110 may be defined as a 3D mesh or other representation and registered to a 3D/4D volumetric data set of the exact same shape. The section is then obtained by sampling the 3D/4D volume over an area defined by the scanning plane 114. In some embodiments, an apparatus 200 may be constructed to submerge an actual object 202 of the desired basic shape inside a medium that can be imaged fey an actual ultrasound 204 or other modalities. The image obtained may be co-registered with 3D geometry to illustrate and record the correlation between sections and corresponding 3D shape.

Choice of Bask Shapes

The basic shapes should be chosen based on their simplicity and similarity to real anatomical structures. In other words, each basic shape 180a-d may be representative of a simplified version of a real anatomical structure. For instance, cones and spheres are widely familiar shapes that are easily understood and students will readily appreciate how their conic sections relate to the global 3D shapes. Cylinders or hollow tubes can be used as a representation of blood vessels or needles. Crossing or bifurcating tubes can be used to represent typical structures that are seen when studying details of actual venal or arterial systems. In additional, the size of the basic shapes should be proportionate to the anatomical structure they represent, so practitioners can get accustomed to their size as they appear on the screen of an ultrasound device.

By way of example only, the basic shapes may include items such as: cone 108b, tube 108d, sphere 108c, and other more complex shapes, such as bifurcating tubes 108a, that may be obtained by combining simpler shapes in a specific 3D arrangement. In some embodiments, the display device may also present the practitioner with a "random" shape life 108e to randomly choose one of the basic shapes or generate a more complex shape. This hides the shape from the user so the user must figure out the shape from the 2D image.

The basic shapes 108a-d may also comprise dynamic characteristics that represent moving structures or movement within a structure (e.g., pulsating or contracting/expanding object), such as structures that are compressible, and structures that demonstrate variations in fluid movement through its internal structure. Each of these shapes may have the ability to pulsate, contract/expand, or have simulated liquid flow through the objects with varying flow characteristics to demonstrate coherent versus turbulent, obstructed, or regurgitant flow characteristics. As an extension, each of these basic shapes 188a-d or other shapes can have additional features or characteristics to simulate movement of or within an anatomical structure.

Figure 3:
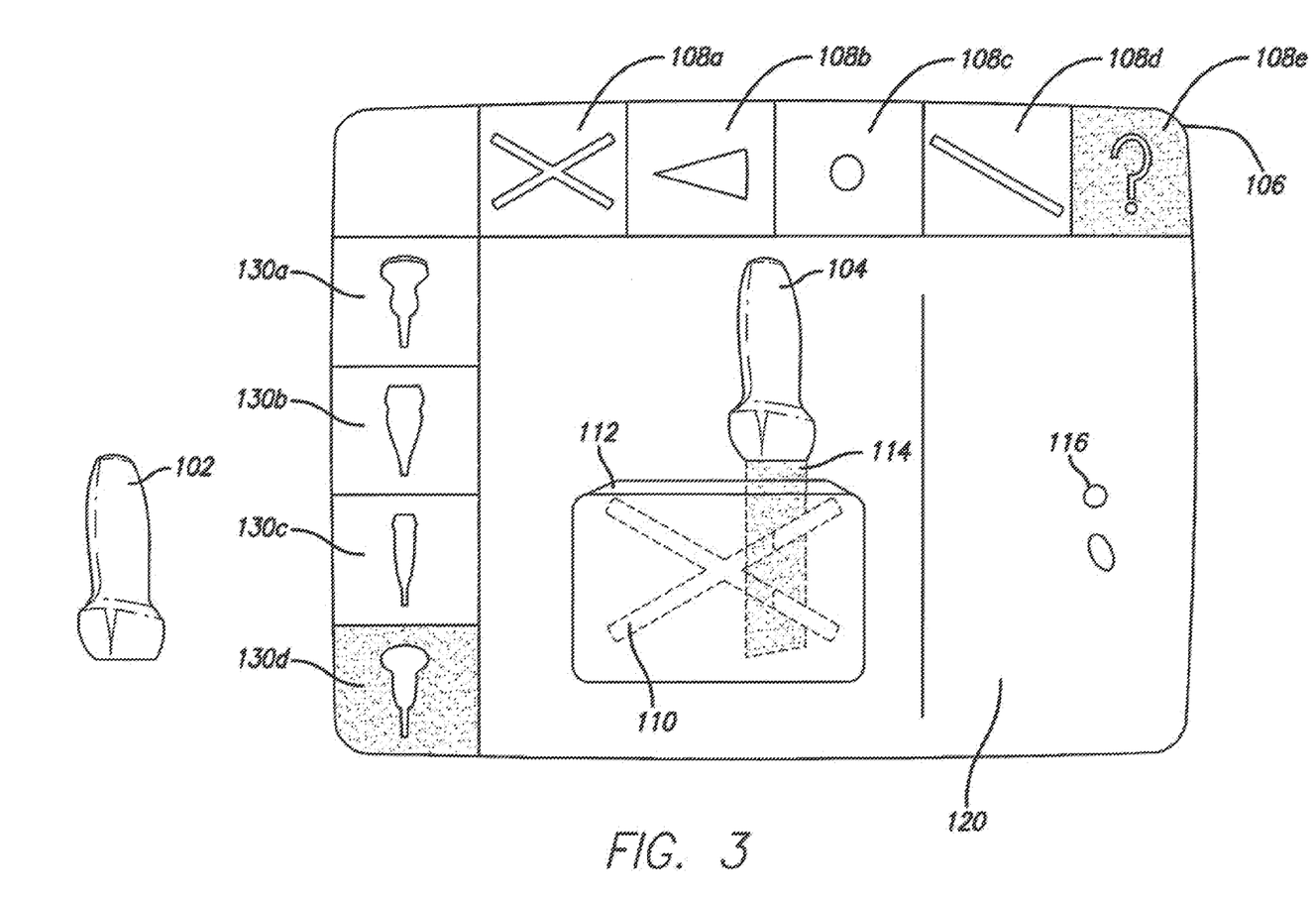
FIG. 3 shows an embodiment of the present invention with the virtual transducer probe cutting through a basic shape that is hidden from the user.

In some embodiments, as shown in FIG. 3, as an additional challenge for the practitioner, on a selection of a random shape 108e, the simulator 100 may at first hide the 3D rendering of a basic shape 110 within an environment 112 that is opaque. The practitioner then scans the opaque environment 112 with the virtual transducer probe 104 by moving the input device 102 until a 2D image is displayed on the display device 106 representing the section cut through by the scanning plane 114 of the virtual transducer probe 104. The practitioner may then be required to determine the 3D shape of the basic object from the 2D section 116 alone. The practitioner can continue scanning the environment 112 and watching the display device 106 to see how the 2D section 116 changes in real-time as the virtual transducer probe 104 is moved. From the 2D information, the practitioner should be able to determine the shapes and orientation of the basic shape in three dimensions. Then at a later time, the practitioner can verify his/her understanding by having the basic shape 110 within the environment 112 revealed. This can be accomplished by either disabling the visualization of the opaque environment 112 altogether to remove the environment 112 or by employing a transparency effect to see through the environment 112.

The practitioner may define the specific characterizations of the basic shape 108a-d and the environment 112 or may simply use a default characterization defined by the system 100. The environment 112 may, for example, represent a portion of the body within which the anatomical structure being examined is contained. In some embodiments, the environment 112 may be depicted as a simple rectangular box, or some other basic shape. In some embodiments, the environment 112 may be contoured to more closely mimic the contours of an actual body, a portion of the body, or a specific body part. In some embodiments, the basic shapes 108a-d may already be associated with a specific anatomical structure. Therefore, selection of the basic body part shape may be accomplished by selecting the anatomical structure the practitioner would like to examine. For example, if the practitioner desires to practice his or her ultrasound technique on a portion of the cardiovascular system, the practitioner may input this anatomical system or select this anatomical system from a list. Once the simulator 100 receives this request, the simulator 100 can either display a basic shape that is supposed to mimic the cardiovascular system, or provide more options to further narrow a specific anatomical structure within the cardiovascular system.

The simulated environment 112 may be analogous to a physical system where a high-density object 202 of the desired shape is immersed inside an apparatus 200 filled with low-density material. Scanning the physical apparatus 200 with a real ultrasound device 204 is expected to produce a result that is similar to the interactions with the simulator 100 as shown in FIG. 4.

Choice of Transducer

New practitioners may be able to select from a series of available virtual transducer probes 130. For example, available virtual transducer probe options may be displayed on the display device 106 for the practitioner to select. Each virtual transducer probe 130a-d represents a real transducer probe and adopts characteristics of the real transducer probe being represented. Therefore, the selected virtual transducer probe 130a-d accurately reflects (in a proportionate and scaled manner) real transducer array signal depth, shape, function, and the like. This allows new practitioners to more appropriately select transducer types for specific ultrasound indications.

Image-Guided Interventions

In some embodiments, additional features may be provided that include introducing simulated image-guided needle interventions. For example, creating a simulated environment in which practitioners acquire the ability to use the selected probe and imagery to guide an instrument, such as a surgical instrument or tool, into an object of interest.

Upon selecting the optimal ultrasound transducer, selecting an ideal image window, and acquiring an optimal image view, new practitioners can perform image-guided interventions. As shown in FIG. 2, the acquired ultrasound image displayed on the display device 106 can be manipulated and used to guide a virtual instrument 105, such as a virtual needle, to its target. This is performed is a safe, simulated environment. It also presents new practitioners with advanced concepts in a gradual manner that facilitates complex psychomotor skill acquisition. A second input device 103 may be required to control the virtual instrument 105 in much the same way the first input device 102 controls the virtual transducer probe 104.

Ultrasound Artifacts

For more advanced practitioners, the visualization of the ultrasound section can be refined to include additional virtual features, such as virtual elements or virtual artifacts that may represent actual ultrasound imaging characteristics, including, but not limited to, beam propagation, speckle noise, shadows, internal reflections, textures that differentiate specific anatomical tissues, Doppler flow characteristics, and the like.

These additional virtual features can be introduced by emulating the physics of ultrasound to incorporate these virtual artifacts directly into a volumetric data set. In some embodiments, these virtual artifacts may be added at runtime using image processing and shading algorithms. In some embodiments, these virtual artifacts can be introduced by constructing and scanning an apparatus 200 containing a medium into which an object 202 of the desired shape and desired characteristics can be submerged that can be imaged by ultrasound 204 or other modalities.

Volumetric Approach

For the volumetric approach, assume that the type of ultrasound transducer 204 (e.g., linear, curvilinear, phased array) and the geometry of the object 202 are known. As explained earlier, the simulated scenario is equivalent to submerging a dense object of the desired shaped into a low-density medium. Applying knowledge of how the beam of the ultrasound transducer propagates in a medium and how it interacts with a given shape, produces a 3D volume shaded in a way that resembles the appearance of a volume acquired with a 3D/4D ultrasound transducer in the equivalent physical setup. Applying this technique to basic shapes demonstrates the effect of ultrasound artifacts in a more abstract and sterile environment. Once a volumetric representation of a basic shape which incorporates the ultrasound artifacts is available, the simulator can then display a 2D image by sampling the volume over the surface of a user-defined slicing plane.

Shading Algorithms

Since the geometries of the basic shapes are known as discussed above. It is also possible to emulate the look of ultrasound directly by applying a shading algorithm to the way a section of the shape is rendered in a graphics engine. For example, a section given as the intersection of the basic shape with the scanning plane is computed. The section of geometry is rendered using a shading algorithm that emulates the appearance of ultrasound at the surface of the basic shape. A noise pattern that resembles the speckle noise of ultrasound is overlaid. Textures that mimic the appearance of real materials viewed with an ultrasound device are also overlaid. The rendering can be integrated in any commercially or freely available graphics engines.

Doppler Flow Characteristics

Ultrasound machines use the Doppler Effect to visualize the presence, direction, and other characteristics of blood flow. When the sonographer enables Doppler visualization, the machine highlights regions of the ultrasound image where there, is an appreciable degree of fluid flow. This feature is very useful for clinicians to identify regions of the body where blood flow is expected (e.g., the aorta), structures that do not carry flowing fluids (e.g., nerves), pathologic conditions where blood or other bodily fluid hemorrhages into nearby structures, and to distinguish veins from arteries based on flow direction and how patterns. Additionally the Doppler Effect can help clinicians estimate certain pathological conditions that originate from constricted or stiff blood vessels, which yield an insufficient blood flow. Most ultrasound machines provide several types of Doppler visualization that aid specific types of clinical applications.

For example, the power Doppler mode is very sensitive to the presence of fluid flow and displays the strength of flow with color intensity. The color flow Doppler mode highlights the direction of flow (e.g. forward or backward) using distinct colors. The pulsed-wave Doppler mode reveals special characteristic of flow that become apparent based on the observed visual pattern and it also helps determine the proximity of structures to the heart.

In order to take advantage of Doppler visualization, new practitioners need to acquire a specialized set of abilities beyond the basic ultrasound skills described earlier. Specifically, they need to further understand; the visual appearance of Doppler visualization, how to interpret Doppler patterns and relate them to the underlying anatomy and/or pathological conditions, when to use Doppler to help study a certain condition, which Doppler mode to use, how to manipulate the transducer to achieve the best views with Doppler enabled.

The present invention can help advanced practitioners understand the use of Doppler visualization in ultrasound imaging by refining the visualization of basic shapes with visual elements that mimic the appearance of Doppler highlights in real ultrasound machines overlaid or incorporated into the represented image. This concept is particularly useful for basic shapes in the form of tubular structures that resemble blood vessels.

There are various ways to emulate Doppler visualisation. A few suggested ways are: using image-processing effects on annotated data; simulating the physics of the Doppler effects based on well-studied notions of Computational Fluid Dynamics (CFD) and the way sound waves propagate into tissues in the presence of flow; and building a physical apparatus that generates fluid flow within basic geometrical shapes and can be scanned with a real ultrasound transducer.

For example, using an image processing approach, ultrasound data may be annotated to identify regions of flow and their characteristics. Image-processing effects may be implemented that emulate the appearance of Doppler visualizations based on flow characteristics.

Using a physics-based approach, a fluid with mechanical properties similar to blood and other bodily fluids may be defined. The geometry of the channels in which the flow is to be constrained as boundary conditions for the CFD solver may be defined. The CFD solver may be ran to determine the field of velocity, pressure, and other physical parameters over the domain of the simulation. The way ultrasound waves, from the transducer interact with the fluid flow may be simulated and changes in the measured frequency of acoustic waves (Doppler effect) recorded. An ultrasound machine translates readings of the Doppler effect into colors simulating and intensities and overlap the colors on the ultrasound, image.

Alternatively, rather than simulating the way ultrasound waves interact with fluid flow and how an ultrasound machine translates readings of the Doppler effect, velocities may be mapped directly to colors and intensities as a simplified way to emulate the appearance of Doppler visualization.

Mechanical Apparatus

In some embodiments, as shown in FIG. 4, an apparatus 200 that showcases fluid flow within a basic geometrically shaped object when scanned with a real ultrasound probe 204 can be built. An engine, motor, compressor, or other hydraulic system can be used to pump fluids with similar viscosity and dynamic properties as blood or other bodily fluids into a pipe system of simple geometry (a single bifurcating tube), or a complex pipe system embedded within object 202. The apparatus 200 can be scanned with a real ultrasound transducer 204. The information acquired can be incorporated into the simulator database for use by the simulator 100 when that basic shape 110 is selected.

The foregoing description of the preferred embodiment of rise invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for teaching practitioners basic ultrasound skills, comprising:
   a. providing a training simulator system, comprising:
      i. an input device to control a virtual ultrasound probe that lets a practitioner determine a position and an orientation of the virtual ultrasound probe proportionate to the position and the orientation of the input device, wherein the input device is a motion-sensing device in the form of a transducer frame that mimics a real ultrasound probe,
      ii. an apparatus containing an object having a basic shape that is scanned by the input device, the basic shape representing an abstraction of an anatomical part;
      iii. a display device comprising a plurality of windows for displaying, during operation, a menu of virtual basic shapes in a first window, a menu of available virtual transducer probes in a second window, the virtual ultrasound probe and a simulated environment in a third window, and a 2D image of a section representing an ultrasound slice in a fourth window;
   b. receiving a user selection of one virtual basic shape from the menu of virtual basic shapes that corresponds with the basic shape of the object within the apparatus, and receiving a user selection of one available virtual transducer probe from the menu of available virtual transducer probes, which corresponds to the input device and the virtual ultrasound probe controlled by the input device;
   c. displaying the virtual ultrasound probe corresponding to the available virtual transducer probe selected and the selected virtual basic shape on the third window of the display device, wherein a scanning plane is emitted from the virtual ultrasound probe through the simulated environment for visualizing a location, a direction, and an orientation of a virtual sound wave;
   d. using the input device in combination with the apparatus to detect the basic shape of the object in the apparatus, wherein the basic shape is selected from a group consisting of cones, conic sections, spheres, cylinders, tubes, crossing tubes, and bifurcating tubes;
   e. receiving instructions from the input device to manipulate the position and the orientation of the virtual ultrasound probe relative to the virtual basic shape to define the ultrasound slice through the virtual basic shape by the scanning plane, wherein movement of the virtual ultrasound probe in three dimensions correlates with movement of the input device in three dimensions; and
   f. displaying in the fourth window of the display device simultaneously with displaying the virtual probe on the third window of the display device, the 2D image of a section of the virtual basic shape defined based on the scanning plane as manipulated by the input device.

2. The method of claim 1, further comprising:
   a. receiving information from the input device to alter the position and orientation of the virtual ultrasound probe;
   b. computing a new ultrasound slice obtained by cutting the virtual basic shape with the scanning plane at the altered position and orientation.

3. The method of claim 1, wherein the virtual basic shape is hidden in the simulated environment, but detectable by the virtual ultrasound probe, such that when the scanning plane intersects the virtual basic shape, the 2D image of the section of the virtual basic shape defined by the ultrasound slice is displayed on the fourth window of the display device.

4. The method of claim 1, further comprising generating virtual artifacts on the fourth window mimicking real artifacts seen in actual ultrasound imaging, wherein the virtual artifacts are generated using a technique selected from the group consisting of a volumetric approach, a shading algorithm, and a Doppler flow characteristic.

5. The method of claim 1, wherein an operation of calculating the scanning plane is further based on the available virtual ultrasound probe selected.

6. The method of claim 1, further comprising providing a second input device operable to define a position and an orientation of a virtual instrument, wherein the operations further comprise receiving the position and the orientation of the virtual instrument from the second input device and displaying the virtual instrument on the third window of the display device.

7. The method of claim 1, wherein the virtual basic shape comprises dynamic characteristics to mimic movement of the anatomical part the virtual basic shape represents.

8. The method of claim 7, wherein the dynamic characteristics comprise at least one of an ability to pulsate, contract and expand, and simulate liquid flow.

9. The method of claim 7, wherein the dynamic characteristics are displayed in the fourth window with the ultrasound slice in different colors.

10. A system for teaching a practitioner basic ultrasound skills, comprising:
    a. an input device to control a virtual ultrasound probe that lets a practitioner define a position and an orientation of the virtual ultrasound probe, wherein the input device is a motion-sensing device in the form of a transducer frame that mimics a real ultrasound probe;
    b. an apparatus containing an object having a basic shape, the basic shape representing an abstraction of an anatomical part;
    c. a display device for displaying, during operation, a menu of virtual basic shapes in a first portion, a menu of available virtual transducer probes in a second portion, a virtual ultrasound probe and a simulated environment in a third portion, and a 2D image of a section representing an ultrasound slice in a fourth portion, wherein the input device controls movement of the virtual ultrasound probe on the display device;
    d. a processor; and
    e. a memory operatively coupled to the processor, the memory storing program instructions that when executed by the processor performs operations to:
       i. display the menu of virtual basic shapes in the first portion of the display device, display the menu of available virtual transducer probes in the second portion of the display device from which a user can select to represent the virtual ultrasound probe, display the selected virtual ultrasound probe in the third portion of the display device, the virtual ultrasound probe emitting a scanning plane from the virtual ultrasound probe for visualizing a location, a direction, and an orientation of a virtual sound wave;

ii. detect the basic shape of the object in the apparatus that is scanned by the input device, the basic shape selected from a group consisting of cones, conic sections, spheres, cylinders, tubes, crossing tubes, and bifurcating tubes, wherein the basic shape corresponds with one virtual basic shape selected from the menu of virtual basic shapes;

iii. display the selected virtual basic shape in the third portion of the display device;

iv. receive instruction from the input device to manipulate the position and the orientation of the virtual ultrasound probe relative to the virtual basic shape to define an ultrasound slice through the virtual basic shape by the scanning, wherein movement of the virtual ultrasound probe in three dimensions correlates with movement of the input device in three dimensions; and v. display the 2D image of the section of the virtual basic shape defined by the ultrasound slice in the fourth portion of the display device.

11. The system of claim 10, wherein the virtual basic shape displayed in the third portion of the display device comprises dynamic characteristics to mimic movement of the anatomical part that the virtual basic shape represents.

12. The system of claim 10, further comprising a second input device operable to define a position and an orientation of a virtual instrument, wherein the operations further comprise receiving the position and the orientation of the virtual instrument from the second input device and displaying the virtual instrument on the third portion of the display device.

13. The system of claim 10, wherein a depiction of the scanning plane is based on the available virtual ultrasound probe selected.

14. The system of claim 10, wherein the virtual basic shape comprises dynamic characteristics to mimic movement of the anatomical part the virtual basic shape represents.

15. The system of claim 14, wherein the dynamic characteristics comprise at least one of an ability to pulsate, contract and expand, and simulate liquid flow.

16. The system of claim 14, wherein the dynamic characteristics are displayed in the fourth window with the ultrasound slice in different colors.

17. The system of claim 10, wherein the operations further comprise generating artifacts in the ultrasound slice to mimic elements that characterize ultrasound imaging.

* * * * *